(12) United States Patent
Schneider et al.

(10) Patent No.: US 6,855,831 B2
(45) Date of Patent: Feb. 15, 2005

(54) PROCESS FOR THE PREPARATION OF CYCLIC DIKETONES

(75) Inventors: Hermann Schneider, Basel (CH); Christoph Lüthy, Basel (CH); Andrew Edmunds, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/409,577

(22) Filed: Apr. 8, 2003

(65) Prior Publication Data

US 2003/0199708 A1 Oct. 23, 2003

(30) Foreign Application Priority Data

Apr. 9, 2002 (CH) .............................................. 598/02

(51) Int. Cl.[7] ..................... C07D 313/16; C07C 207/00; C07C 49/613

(52) U.S. Cl. ..................... 549/271; 568/307; 568/375; 568/376

(58) Field of Search ................................ 568/307, 375, 568/376; 549/271

(56) References Cited

FOREIGN PATENT DOCUMENTS

| EP | 0186117 | | 7/1986 |
|---|---|---|---|
| WO | 00/15615 | | 3/2000 |
| WO | 0015615 | * | 3/2000 |
| WO | 00/37437 | | 6/2000 |
| WO | 037437 | * | 6/2000 |
| WO | 01/66522 | | 9/2001 |
| WO | 0166533 | * | 9/2001 |
| WO | 01/94339 | | 12/2001 |

OTHER PUBLICATIONS

Ca 140:42184, "Preparation of herbicidally active nicotinoyl derivatives", Luethy et. al., WO2003106448.*

* cited by examiner

*Primary Examiner*—Cecilia J. Tsang
*Assistant Examiner*—Binta Robinson
(74) *Attorney, Agent, or Firm*—Thomas Hamilton

(57) ABSTRACT

The present invention relates to a process for the preparation of compounds of formula I:

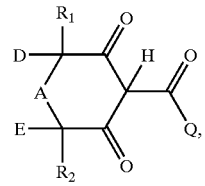

(I)

wherein the substituents are as defined in claim 1, by conversion of a compound of formula II:

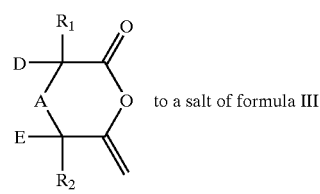

(II)

to a salt of formula III

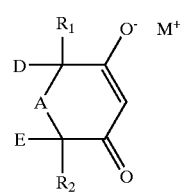

(III)

reaction of that compound with a compound of formula IV:

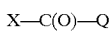

X—C(O)—Q    (IV), wherein X is a leaving group, to form a compound of formula V:

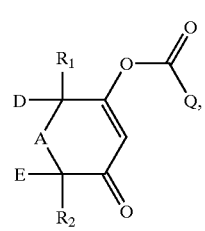

(V)

and treatment of that compound in the presence of a base with catalytic amounts of cyanide ions.

1 Claim, No Drawings

PROCESS FOR THE PREPARATION OF CYCLIC DIKETONES

The present invention relates to a process for the preparation of cyclic 1,3-diketone derivatives carbonylated in the 2-position.

Processes for the preparation of cyclic 1,3-diketones substituted in the 2-position by an arylcarbonyl group are described, for example, in WO 00/15615, WO 00/37437, WO 01/66522 and WO 01/94339. Those compounds have herbicidal action.

Those processes have the disadvantage, however, that some cyclic 1,3-diketone starting compounds unsubstituted in the 2-position, especially the bicyclic 1,3-diketone starting compounds, are generally not readily obtainable, and derivatives thereof can usually be prepared only by way of a number of complex synthesising steps and purification procedures.

In addition, in the known processes the isolation of the end products, especially in the case of 2-benzoyl, 2-pyridylcarbonyl and 2-heteroarylcarbonyl derivatives, is associated with high expenditure, since it generally involves a multi-stage procedure. The purity and yield of the cyclic 1,3-diketones prepared according to the known processes are accordingly frequently unsatisfactory.

The aim of the present invention is therefore to provide a novel general process for the preparation of monocyclic and bicyclic 1,3-diketone derivatives, especially 2-benzoyl, 2-isonicotinoyl and 2-nicotinoyl derivatives, by means of which it is possible to prepare such compounds in high yields and good quality, by a simple reaction procedure and with low expenditure, without the above-mentioned disadvantages of the known processes.

The present invention accordingly relates to a process for the preparation of compounds of formula I:

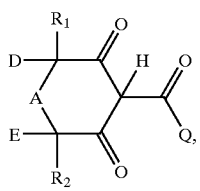
(I)

wherein Q is an organic substituent so selected that the compound of formula I has a pK value of from 1 to 5;

D is hydrogen or $R_3$;

E is hydrogen or $R_4$; or

D and E together are $C_2$–$C_3$alkylene, which may be mono- or poly-substituted by $R_6$;

A is $C_1$–$C_2$alkylene, which may be mono- or poly-substituted by $R_5$; or, when D and E are other than $C_2$–$C_3$alkylene, A may additionally be carbonyl, oxygen or —$NR_7$—;

$R_1$, $R_2$, $R_3$, $R_4$, $R_5$ and $R_6$ are each independently of the others hydrogen, $C_1$–$C_4$alkyl, phenyl, $C_1$–$C_4$alkoxy, halogen, hydroxy, cyano, hydroxycarbonyl or $C_1$–$C_4$alkoxycarbonyl; and $R_7$ is $C_1$–$C_4$alkyl, alkoxycarbonyl or $C_1$–$C_4$alkylcarbonyl, which process comprises a) converting a compound of formula II

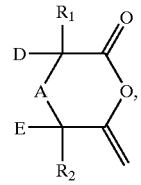
(II)

wherein $R_1$, $R_2$, A, D and E are as defined for formula I, either in the presence of an amine base and a catalytic amount of a cyanide or in the presence of an alkali metal alcoholate or alkaline earth metal alcoholate, to a salt of formula III:

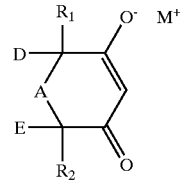
(III)

wherein $R_1$, $R_2$, A, D and E are as defined for formula I and $M^+$ is an alkali metal ion, alkaline earth metal ion or ammonium ion, b) reacting that compound with a compound of formula IV:

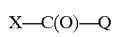

X—C(O)—Q  (IV), wherein X is a leaving group and Q is as defined for formula I, to yield a compound of formula V:

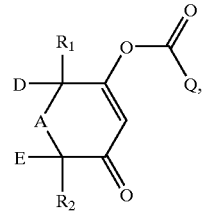
(V)

wherein $R_1$, $R_2$, A, D, E and Q are as defined for formula I, and c) converting that compound in the presence of catalytic amounts of cyanide ions and in the presence of a base to a compound of formula I.

Since the compounds of formula I are preferably in enolised forms or in the form of salts, the process according to the invention also includes the preparation of those enolised forms of formulae Ia, Ib, Ic and Id wherein $Me^+$ is hydrogen or an alkali metal ion, alkaline earth metal ion or ammonium ion:

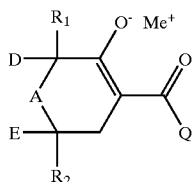

(Ia)

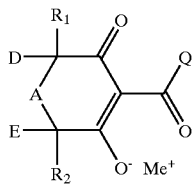

(Ib)

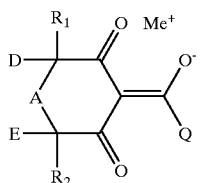

(Ic)

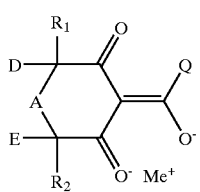

(Id)

Since it is also possible for asymmetric carbon atoms to be present in compounds of formula I, for example in the case of the carbon atom carrying $R_1$, D and A, all stereoisomeric forms are also included. This applies correspondingly also to all possible tautomeric and stereoisomeric forms of the compounds of formulae II, III, IV and V used as intermediates.

Q is especially an organic substituent so selected that the compound of formula I has a pK value of from 2.5 to 4.

The organic substituent Q may be a substituent of any structure, provided that it is substantially inert under the reaction conditions of the process according to the invention.

Q is preferably a mono- or poly-substituted phenyl, pyridyl or heteroaryl group, especially a di- or tri-substituted phenyl group, or a disubstituted 2-pyridyl or 3-pyridyl group, the substitution pattern for such groups being freely selectable with the proviso that such groups are substantially inert under the reaction conditions of the process according to the invention. Preference is given to the phenyl, 3-pyridyl and heteroaryl groups that carry at least one substituent, which is especially preferably in the ortho position.

There may especially advantageously be prepared according to the process of the invention compounds of formula I wherein Q is:

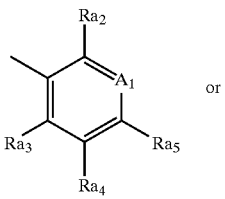

(Q₁)

or

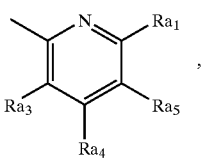

(Q₂)

wherein:

$A_1$ is $CRa_1$ or $N-(O)_p$;

p is 0 or 1;

$Ra_1$ is hydrogen, $C_1-C_6$alkyl, hydroxy, $C_1-C_6$alkoxy, $C_1-C_6$haloalkoxy, $C_3-C_6$alkenyloxy, $C_3-C_6$haloalkenyloxy, $C_3-C_6$alkynyloxy, $C_1-C_4$alkylcarbonyloxy, $C_1-C_4$alkylsulfonyloxy, phenylsulfonyloxy, $C_1-C_6$alkylthio, $C_1-C_6$alkylsulfinyl, $C_1-C_6$alkylsulfonyl, $C_1-C_6$alkylamino, di($C_1-C_6$alkyl)amino, $C_1-C_3$alkoxy-$C_1-C_3$alkylamino, $C_1-C_3$alkoxy-$C_1-C_3$alkyl-N($C_1-C_3$alkyl)-, $C_1-C_4$alkoxycarbonyl, $C_1-C_6$haloalkyl, formyl, cyano, halogen, phenyl or phenoxy, wherein the phenyl-containing groups may themselves be substituted by $C_1-C_3$alkyl, $C_1-C_3$haloalkyl, $C_1-C_3$alkoxy, $C_1-C_3$haloalkoxy, halogen, cyano or by nitro;

or $Ra_1$ is a three- to ten-membered monocyclic or, together with $Ra_2$ or $Ra_5$, fused bicyclic ring system, which may be interrupted once or up to three times by heterocyclic substituents selected from oxygen, sulfur, S(O), $SO_2$, $N(Ra_6)$, carbonyl and $C(=NORa_7)$, and wherein, when the ring system is not fused, it is bonded to the carbon atom of the substituent $A_1$, either directly or by way of a $C_1-C_4$alkylene, $C_2-C_4$alkenylene or $C_2-C_4$alkynylene bridge which may be interrupted by oxygen, $-N(C_1-C_4$alkyl)-, sulfur, sulfinyl or by sulfonyl, and the ring system may contain no more than two oxygen atoms and no more than two sulfur atoms, and the ring system may itself be mono-, di- or tri-substituted by $C_1-C_6$alkyl, $C_1-C_6$haloalkyl, $C_2-C_6$alkenyl, $C_2-C_6$haloalkenyl, $C_2-C_6$alkynyl, $C_2-C_6$haloalkynyl, $C_1-C_6$alkoxy, $C_1-C_6$haloalkoxy, $C_3-C_6$alkenyloxy, $C_3-C_6$alkynyloxy, $C_1-C_6$alkylthio, $C_1-C_6$haloalkylthio, $C_3-C_6$alkenylthio, $C_3-C_6$haloalkenylthio, $C_3-C_6$alkynylthio, $C_1-C_4$alkoxy-$C_1-C_2$alkylthio, $C_1-C_4$alkylcarbonyl-$C_1-C_2$alkylthio, $C_1-C_4$alkoxycarbonyl-$C_1-C_2$alkylthio, cyano-$C_1-C_4$alkylthio, $C_1-C_6$alkylsulfinyl, $C_1-C_6$haloalkylsulfinyl, $C_1-C_6$alkylsulfonyl, $C_1-C_6$haloalkylsulfonyl, aminosulfonyl, $C_1-C_4$alkylaminosulfonyl, di($C_1-C_4$alkyl)aminosulfonyl, di($C_1-C_4$alkyl)amino, halogen, cyano, nitro, phenyl, benzyloxy and/or by benzylthio, and wherein the phenyl-containing groups may themselves be substituted on the phenyl ring by $C_1-C_3$alkyl, $C_1-C_3$haloalkyl, $C_1-C_3$alkoxy, $C_1-C_3$haloalkoxy, halogen, cyano or by nitro, and wherein substituents on the nitrogen in the heterocyclic ring are other than halogen;

or $Ra_1$ is the group $-X_5-X_7$ or the group $-X_6-X_5-X_7$; wherein $X_5$ is oxygen, $-O(CO)-$, $-(CO)O-$, $-O(CO)O-$, $-N(C_1-C_4$alkyl)-O-, $-O-N(C_1-C_4$alkyl)-, sulfur, sulfinyl, sulfonyl, —SO$_2$N(C$_1$–C$_4$alkyl)-, —N(C$_1$–C$_4$alkyl)SO$_2$—, —N(C$_1$–C$_2$alkoxy-C$_1$–C$_2$alkyl)SO$_2$— or —N(C$_1$–C$_4$alkyl)-;

X$_6$ is a C$_1$–C$_6$alkylene, C$_3$–C$_6$alkenylene or C$_3$–C$_6$alkynylene chain, which may be mono- or poly-substituted by halogen or by X$_8$, the unsaturated bonds of the chain not being bonded directly to the substituent X$_5$;

Ra$_6$ is hydrogen, C$_1$–C$_4$alkyl, C$_1$–C$_4$alkylthio-C$_1$–C$_4$alkylcarbonyl, C$_1$–C$_4$alkylsulfinyl-C$_1$–C$_4$alkylcarbonyl, C$_1$–C$_4$alkylsulfonyl-C$_1$–C$_4$alkylcarbonyl, C$_1$–C$_4$alkoxycarbonyl, C$_1$–C$_4$alkylcarbonyl, phenylcarbonyl or phenyl, wherein the phenyl groups may themselves be substituted by C$_1$–C$_4$alkyl, C$_1$–C$_4$haloalkyl, C$_1$–C$_4$alkoxy, C$_1$–C$_4$haloalkoxy, C$_1$–C$_4$alkylcarbonyl, C$_1$–C$_4$alkoxycarbonyl, C$_1$–C$_4$alkylamino, di(C$_1$–C$_4$alkyl)amino, C$_1$–C$_4$alkylthio, C$_1$–C$_4$alkylsulfinyl, C$_1$–C$_4$alkyl-SO$_2$, C$_1$–C$_4$alkyl-S(O)$_2$O, C$_1$–C$_4$haloalkylthio, C$_1$–C$_4$haloalkylsulfinyl, C$_1$–C$_4$haloalkyl-SO$_2$, C$_1$–C$_4$haloalkyl-S(O)$_2$O, C$_1$–C$_4$alkyl-S(O)$_2$NH, C$_1$–C$_4$alkyl-S(O)$_2$N(C$_1$–C$_4$alkyl)-, halogen, nitro or by cyano;

Ra$_7$ is hydrogen, C$_1$–C$_4$alkyl, C$_3$–C$_4$alkenyl, C$_3$–C$_4$alkynyl or benzyl;

Ra$_2$ is hydrogen, C$_1$–C$_6$alkyl, C$_1$–C$_6$haloalkyl, C$_2$–C$_6$alkenyl, C$_2$–C$_6$haloalkenyl, C$_1$–C$_2$alkoxycarbonyl- or phenyl-substituted vinyl, C$_2$–C$_6$alkynyl, C$_2$–C$_6$haloalkynyl, trimethylsilyl-, hydroxy-, C$_1$–C$_6$alkoxy-, C$_1$–C$_4$alkoxycarbonyl- or phenyl-substituted ethynyl, C$_3$–C$_6$allenyl, C$_3$–C$_6$cycloalkyl, halo- or C$_1$–C$_3$alkoxymethyl-substituted C$_3$–C$_6$cycloalkyl, C$_1$–C$_6$alkoxy, C$_3$–C$_6$alkenyloxy, C$_3$–C$_6$alkynyloxy, C$_1$–C$_6$haloalkoxy, C$_3$–C$_6$haloalkenyloxy, cyano-C$_1$–C$_4$alkoxy, C$_1$–C$_4$alkoxy-C$_1$–C$_4$alkoxy, C$_1$–C$_4$alkylthio-C$_1$–C$_4$alkoxy, C$_1$–C$_4$alkylsulfinyl-C$_1$–C$_4$alkoxy, C$_1$–C$_4$alkylsulfonyl-C$_1$–C$_4$alkoxy, C$_1$–C$_4$alkoxycarbonyl-C$_1$–C$_4$alkoxy, C$_1$–C$_6$alkylthio, C$_1$–C$_6$alkylsulfinyl, C$_1$–C$_6$alkylsulfonyl, C$_1$–C$_6$haloalkylthio, C$_1$–C$_6$haloalkylsulfinyl, C$_1$–C$_6$haloalkylsulfonyl, C$_1$–C$_4$alkoxycarbonyl-C$_1$–C$_4$alkylthio, C$_1$–C$_4$alkoxycarbonyl-C$_1$–C$_4$alkylsulfinyl, C$_1$–C$_4$alkoxycarbonyl-C$_1$–C$_4$alkylsulfonyl, C$_1$–C$_6$alkylamino, di(C$_1$–C$_6$alkyl)amino, C$_1$–C$_3$alkoxy-C$_1$–C$_3$alkylamino, C$_1$–C$_3$alkoxy-C$_1$–C$_3$alkyl-N(C$_1$–C$_3$alkyl), C$_1$–C$_6$alkylaminosulfonyl, di(C$_1$–C$_6$alkyl)aminosulfonyl, C$_1$–C$_4$alkylsulfonyloxy, C$_1$–C$_4$haloalkylsulfonyloxy, C$_1$–C$_4$alkylsulfonylamino, C$_1$–C$_4$alkylsulfonyl-N(C$_1$–C$_4$alkyl), cyano, carbamoyl, C$_1$–C$_4$alkoxycarbonyl, formyl, halogen, rhodano, amino, hydroxy-C$_1$–C$_4$alkyl, C$_1$–C$_4$alkoxy-C$_1$–C$_4$alkyl, C$_1$–C$_4$alkylthio-C$_1$–C$_4$alkyl, C$_1$–C$_4$alkylsulfinyl-C$_1$–C$_4$alkyl, C$_1$–C$_4$alkylsulfonyl-C$_1$–C$_4$alkyl, cyano-C$_1$–C$_4$alkyl, C$_1$–C$_6$alkylcarbonyloxy-C$_1$–C$_4$alkyl, C$_1$–C$_4$alkoxycarbonyl-C$_1$–C$_4$alkyl, C$_1$–C$_4$alkoxycarbonyloxy-C$_1$–C$_4$alkyl, rhodano-C$_1$–C$_4$alkyl, phenyl-C$_1$–C$_4$alkyl, phenoxy-C$_1$–C$_4$alkyl, benzyloxy-C$_1$–C$_4$alkyl, benzoyloxy-C$_1$–C$_4$alkyl, (2-oxiranyl)-C$_1$–C$_4$alkyl, C$_1$–C$_4$alkylamino-C$_1$–C$_4$alkyl, di(C$_1$–C$_4$alkyl)-amino-C$_1$–C$_4$alkyl, C$_1$–C$_{12}$alkylthiocarbonyl-C$_1$–C$_4$alkyl or formyl-C$_1$–C$_4$alkyl, or benzylthio, benzylsulfinyl, benzylsulfonyl, benzyloxy, benzyl, phenyl, phenoxy, phenylthio, phenylsulfinyl or phenylsulfonyl, wherein the phenyl-containing groups may themselves be substituted by C$_1$–C$_3$alkyl, C$_1$–C$_3$haloalkyl, C$_1$–C$_3$alkoxy, C$_1$–C$_3$haloalkoxy, halogen, cyano or by nitro; or Ra$_2$ is a three- to ten-membered monocyclic or fused bicyclic ring system, which may be aromatic, saturated or partially saturated and may contain from 1 to 4 hetero atoms selected from nitrogen, oxygen and sulfur, wherein the ring system is bonded to the group Q$_1$ or Q$_2$ by way of a C$_1$–C$_4$alkylene, C$_2$–C$_4$alkenylene or C$_2$–C$_4$alkynylene bridge which may be interrupted by oxygen, —N(C$_1$–C$_4$alkyl)-, sulfur, sulfinyl, sulfonyl or by carbonyl, and each ring system may contain no more than two oxygen atoms and no more than two sulfur atoms, and the ring system may itself be mono-, di- or tri-substituted by C$_1$–C$_6$alkyl, C$_1$–C$_6$haloalkyl, C$_2$–C$_6$alkenyl, C$_2$–C$_6$haloalkenyl, C$_2$–C$_6$alkynyl, C$_2$–C$_6$haloalkynyl, C$_1$–C$_6$alkoxy, C$_1$–C$_6$haloalkoxy, C$_3$–C$_6$alkenyloxy, C$_3$–C$_6$alkynyloxy, hydroxy, mercapto, C$_1$–C$_6$alkylthio, C$_1$–C$_6$haloalkylthio, C$_3$–C$_6$alkenylthio, C$_3$–C$_6$haloalkenylthio, C$_3$–C$_6$alkynylthio, C$_1$–C$_4$alkoxy-C$_1$–C$_3$alkylthio, C$_1$–C$_4$alkylcarbonyl-C$_1$–C$_3$alkylthio, C$_1$–C$_4$alkoxycarbonyl-C$_1$–C$_3$alkylthio, cyano-C$_1$–C$_3$alkylthio, C$_1$–C$_6$alkylsulfinyl, C$_1$–C$_6$haloalkylsulfinyl, C$_1$–C$_6$alkylsulfonyl, C$_1$–C$_6$haloalkylsulfonyl, aminosulfonyl, C$_1$–C$_4$alkylaminosulfonyl, di(C$_1$–C$_4$alkyl)aminosulfonyl, di(C$_1$–C$_4$alkyl)amino, halogen, cyano, nitro, phenyl and/or by benzylthio, wherein phenyl and benzylthio may themselves be substituted on the phenyl ring by C$_1$–C$_3$alkyl, C$_1$–C$_3$haloalkyl, C$_1$–C$_3$alkoxy, C$_1$–C$_3$haloalkoxy, halogen, cyano or by nitro, and wherein substituents on the nitrogen in the heterocyclic ring are other than halogen; or Ra$_2$ is the group —X$_1$—X$_3$ or the group —X$_2$—X$_1$—X$_3$; wherein X$_1$ is oxygen, —O(CO)—, —(CO)O—, —O(CO)O—, —N(C$_1$–C$_4$alkyl)-O—, —O—N(C$_1$–C$_4$alkyl)-, thio, sulfinyl, sulfonyl, —SO$_2$N(C$_1$–C$_4$alkyl)-, —N(C$_1$–C$_4$alkyl)SO$_2$—, —N(C$_1$–C$_2$alkoxy-C$_1$–C$_2$alkyl)SO$_2$— or —N(C$_1$–C$_4$alkyl)-;

X$_2$ is a C$_1$–C$_6$alkylene, C$_3$–C$_6$alkenylene or C$_3$–C$_6$alkynylene chain, which may be mono- or poly-substituted by halogen or by X$_4$, the unsaturated bonds of the chain not being bonded directly to the substituent X$_1$;

X$_3$ and X$_7$ are each independently of the other a C$_1$–C$_8$alkyl, C$_3$–C$_6$alkenyl or C$_3$–C$_6$alkynyl group, which may be mono- or poly-substituted by halogen, hydroxy, amino, formyl, nitro, cyano, mercapto, carbamoyl, C$_1$–C$_6$alkoxy, C$_1$–C$_6$alkoxycarbonyl, C$_2$–C$_6$alkenyl, C$_2$–C$_6$haloalkenyl, C$_2$–C$_6$alkynyl, C$_2$–C$_6$haloalkynyl, C$_3$–C$_6$cycloalkyl, halo-substituted C$_3$–C$_6$cycloalkyl, C$_3$–C$_6$alkenyloxy, C$_3$–C$_6$alkynyloxy, C$_1$–C$_6$haloalkoxy, C$_3$–C$_6$haloalkenyloxy, cyano-C$_1$–C$_6$alkoxy, C$_1$–C$_6$alkoxy-C$_1$–C$_6$alkoxy, C$_1$–C$_6$alkoxy-C$_1$–C$_6$alkoxy-C$_1$–C$_6$alkoxy, C$_1$–C$_6$alkylthio-C$_1$–C$_6$alkoxy, C$_1$–C$_6$alkylsulfinyl-C$_1$–C$_6$alkoxy, C$_1$–C$_6$alkylsulfonyl-C$_1$–C$_6$alkoxy, C$_1$–C$_6$alkoxycarbonyl-C$_1$–C$_6$alkoxy, C$_1$–C$_6$alkoxycarbonyl, C$_1$–C$_6$alkylcarbonyl, C$_1$–C$_6$alkylthio, C$_1$–C$_6$alkylsulfinyl, C$_1$–C$_6$alkylsulfonyl, C$_1$–C$_6$haloalkylthio, C$_1$–C$_6$haloalkylsulfinyl, C$_1$–C$_6$haloalkylsulfonyl, oxiranyl which may itself be substituted by C$_1$–C$_6$alkyl, (3-oxetanyl)-oxy which may itself be substituted by C$_1$–C$_6$alkyl, benzyloxy, benzylthio, benzylsulfinyl, benzylsulfonyl, C$_1$–C$_6$alkylamino, di(C$_1$–C$_6$alkyl)amino, C$_1$–C$_4$alkyl-S(O)$_2$O, di(C$_1$–C$_4$alkyl)aminosulfonyl, rhodano, phenyl, phenoxy, phenylthio, phenylsulfinyl or by phenylsulfonyl, and wherein the phenyl- or benzyl-containing groups may themselves be substituted by one or more C$_1$–C$_6$alkyl, C$_1$–C$_6$haloalkyl, C$_1$–C$_6$alkoxy, C$_1$–C$_6$haloalkoxy, halogen, cyano, hydroxy or nitro groups; or X$_3$ and X$_7$ are each independently of the other phenyl, which may be mono- or poly-substituted by C$_1$–C$_6$alkyl, C$_1$–C$_6$haloalkyl, C$_1$–C$_6$alkoxy, C$_1$–C$_6$haloalkoxy, halogen, cyano, hydroxy or by nitro; or $X_3$ and $X_7$ are each independently of the other $C_3$–$C_6$cycloalkyl, $C_1$–$C_6$alkoxy- or $C_1$–$C_6$alkyl-substituted $C_3$–$C_6$cycloalkyl, 3-oxetanyl or $C_1$–$C_6$alkyl-substituted 3-oxetanyl; or $X_3$ and $X_7$ are each independently of the other a three- to ten-membered monocyclic or fused bicyclic ring system, which may be aromatic, saturated or partially saturated and may contain from 1 to 4 hetero atoms selected from nitrogen, oxygen and sulfur, wherein the ring system is bonded to the substituent $X_1$ or $X_5$ directly or by way of a $C_1$–$C_4$alkylene, $C_2$–$C_4$alkenylene, $C_2$–$C_4$alkynylene, —N($C_1$–$C_4$alkyl)-$C_1$–$C_4$alkylene, —S(O)—$C_1$–$C_4$alkylene or —$SO_2$—$C_1$–$C_4$alkylene group, and each ring system may contain no more than two oxygen atoms and no more than two sulfur atoms, and the ring system may itself be mono-, di- or tri-substituted by $C_1$–$C_6$alkyl, $C_1$–$C_6$haloalkyl, $C_2$–$C_6$alkenyl, $C_2$–$C_6$haloalkenyl, $C_2$–$C_6$alkynyl, $C_2$–$C_6$haloalkynyl, $C_1$–$C_6$alkoxy, hydroxy, $C_1$–$C_6$haloalkoxy, $C_3$–$C_6$alkenyloxy, $C_3$–$C_6$alkynyloxy, mercapto, $C_1$–$C_6$alkylthio, $C_1$–$C_6$haloalkylthio, $C_3$–$C_6$alkenylthio, $C_3$–$C_6$haloalkenylthio, $C_3$–$C_6$alkynylthio, $C_1$–$C_3$alkoxy-$C_1$–$C_3$alkylthio, $C_1$–$C_4$alkylcarbonyl-$C_1$–$C_2$alkylthio, $C_1$–$C_4$alkoxycarbonyl-$C_1$–$C_2$alkylthio, cyano-$C_1$–$C_3$alkylthio, $C_1$–$C_6$alkylsulfinyl, $C_1$–$C_6$haloalkylsulfinyl, $C_1$–$C_6$alkylsulfonyl, $C_1$–$C_6$haloalkylsulfonyl, aminosulfonyl, $C_1$–$C_2$alkylaminosulfonyl, di($C_1$–$C_2$alkyl)aminosulfonyl, di($C_1$–$C_4$alkyl)amino, $C_1$–$C_6$carbonylamino, halogen, cyano, nitro, phenyl, benzyloxy and/or by benzylthio, wherein the phenyl groups may themselves be substituted on the phenyl ring by $C_1$–$C_3$alkyl, $C_1$–$C_3$haloalkyl, $C_1$–$C_3$alkoxy, $C_1$–$C_3$haloalkoxy, halogen, cyano or by nitro, and wherein the substituents on the nitrogen in the heterocyclic ring are other than halogen; and $X_4$ and $X_8$ are each independently of the other hydroxy, $C_1$–$C_6$alkoxy, ($C_3$–$C_6$cycloalkyl)oxy, $C_1$–$C_6$alkoxy-$C_1$–$C_6$alkoxy, $C_1$–$C_6$alkoxy-$C_1$–$C_6$alkoxy-$C_1$–$C_6$alkoxy or $C_1$–$C_6$alkylsulfonyloxy;

$Ra_3$ is hydrogen, $C_1$–$C_6$alkyl, $C_1$–$C_6$haloalkyl, $C_2$–$C_6$alkenyl, $C_2$–$C_6$haloalkenyl, $C_2$–$C_6$alkynyl, $C_2$–$C_6$haloalkynyl, $C_3$–$C_6$cycloalkyl, $C_1$–$C_6$alkoxy, $C_1$–$C_6$haloalkoxy, $C_1$–$C_6$alkylthio, $C_1$–$C_6$alkylsulfinyl, $C_1$–$C_6$alkylsulfonyl, $C_1$–$C_6$haloalkylthio, $C_1$–$C_6$haloalkylsulfinyl, $C_1$–$C_6$haloalkylsulfonyl, amino, $C_1$–$C_6$alkylamino, di($C_1$–$C_6$alkyl)amino, $C_1$–$C_4$alkylsulfonyl-N($C_1$–$C_4$alkyl)-, $C_1$–$C_6$alkylaminosulfonyl, di($C_1$–$C_6$alkyl)aminosulfonyl, cyano, halogen, $C_1$–$C_4$alkoxy-$C_1$–$C_4$alkyl, $C_1$–$C_4$alkylthio-$C_1$–$C_4$alkyl, $C_1$–$C_4$alkylsulfinyl-$C_1$–$C_4$alkyl, $C_1$–$C_4$alkylsulfonyl-$C_1$–$C_4$alkyl, phenyl, phenylthio, phenylsulfinyl, phenylsulfonyl or phenoxy, wherein phenyl groups may themselves be substituted by $C_1$–$C_3$alkyl, $C_1$–$C_3$haloalkyl, $C_1$–$C_3$alkoxy, $C_1$–$C_3$haloalkoxy, halogen, cyano or by nitro;

$Ra_4$ is hydrogen, $C_1$–$C_6$alkyl, hydroxy, $C_1$–$C_6$alkoxy, $C_1$–$C_6$haloalkoxy, $C_3$–$C_6$alkenyloxy, $C_3$–$C_6$haloalkenyloxy, $C_3$–$C_6$alkynyloxy, $C_1$–$C_4$alkylcarbonyloxy, $C_1$–$C_4$alkylsulfonyloxy, phenylsulfonyloxy, $C_1$–$C_4$alkylthio, $C_1$–$C_4$alkylsulfinyl, $C_1$–$C_4$alkylsulfonyl, $C_1$–$C_4$alkylamino, di($C_1$–$C_4$alkyl)amino, $C_1$–$C_4$alkoxycarbonyl, $C_1$–$C_4$haloalkyl, formyl, cyano, halogen, phenyl or phenoxy, wherein the phenyl-containing groups may themselves be substituted by $C_1$–$C_3$alkyl, $C_1$–$C_3$haloalkyl, $C_1$–$C_3$alkoxy, $C_1$–$C_3$haloalkoxy, halogen, cyano or by nitro; or $Ra_4$ is a three- to ten-membered monocyclic or, together with $Ra_3$ or $Ra_5$, fused bicyclic ring system, which may contain from 1 to 4 hetero atoms selected from nitrogen, oxygen and sulfur, wherein, when the ring system is not fused, it is bonded to the group $Q_1$ or $Q_2$, either directly or by way of a $C_1$–$C_4$alkylene, $C_2$–$C_4$alkenylene or $C_2$–$C_4$alkynylene bridge which may be interrupted by oxygen, —N($C_1$–$C_4$alkyl)-, sulfur, sulfinyl, sulfonyl or by carbonyl, and the ring system may contain no more than two oxygen atoms and no more than two sulfur atoms, and the ring system may itself be mono-, di- or tri-substituted by $C_1$–$C_6$alkyl, $C_1$–$C_6$haloalkyl, $C_2$–$C_6$alkenyl, $C_2$–$C_6$haloalkenyl, $C_2$–$C_6$alkynyl, $C_2$–$C_6$haloalkynyl, $C_1$–$C_6$alkoxy, $C_1$–$C_6$haloalkoxy, $C_3$–$C_6$alkenyloxy, $C_3$–$C_6$alkynyloxy, $C_1$–$C_6$alkylthio, $C_1$–$C_6$haloalkylthio, $C_3$–$C_6$alkenyl-thio, $C_3$–$C_6$haloalkenylthio, $C_3$–$C_6$alkynyl-thio, $C_1$–$C_4$alkoxy-$C_1$–$C_2$alkylthio, $C_1$–$C_4$alkylcarbonyl-$C_1$–$C_2$alkylthio, $C_1$–$C_4$alkoxycarbonyl-$C_1$–$C_2$alkylthio, cyano-$C_1$–$C_4$alkylthio, $C_1$–$C_6$alkylsulfinyl, $C_1$–$C_6$haloalkylsulfinyl, $C_1$–$C_6$alkylsulfonyl, $C_1$–$C_6$haloalkylsulfonyl, aminosulfonyl, $C_1$–$C_4$alkylaminosulfonyl, di($C_1$–$C_4$alkyl)aminosulfonyl, amino, $C_1$–$C_4$alkylamino, di($C_1$–$C_4$alkyl)-amino, halogen, cyano, nitro, phenyl and by/or benzylthio, wherein phenyl and benzylthio may themselves be substituted on the phenyl ring by $C_1$–$C_3$alkyl, $C_1$–$C_3$haloalkyl, $C_1$–$C_3$alkoxy, $C_1$–$C_3$haloalkoxy, halogen, cyano or by nitro, and wherein substituents on the nitrogen in the heterocyclic ring are other than halogen;

$Ra_5$ is hydrogen, $C_1$–$C_6$alkyl, $C_1$–$C_6$haloalkyl, $C_2$–$C_6$alkenyl, $C_2$–$C_6$haloalkenyl, $C_2$–$C_6$alkynyl, $C_2$–$C_6$haloalkynyl, $C_3$–$C_6$cycloalkyl, $C_1$–$C_6$alkoxy, $C_1$–$C_6$haloalkoxy, $C_1$–$C_6$alkylthio, $C_1$–$C_6$alkylsulfinyl, $C_1$–$C_6$alkylsulfonyl, $C_1$–$C_6$haloalkylthio, $C_1$–$C_6$haloalkylsulfinyl, $C_1$–$C_6$haloalkylsulfonyl, $C_1$–$C_6$alkylsulfonyloxy, hydroxy, mercapto, amino, $C_1$–$C_6$alkylamino, di($C_1$–$C_6$alkyl)amino, $C_1$–$C_4$alkylsulfonylamino, $C_1$–$C_4$alkylsulfonyl-N($C_1$–$C_4$alkyl)-, $C_1$–$C_6$alkylaminosulfonyl, di($C_1$–$C_6$alkyl)aminosulfonyl, cyano, halogen, $C_1$–$C_4$alkoxy-$C_1$–$C_4$alkyl, $C_1$–$C_4$alkylthio-$C_1$–$C_4$alkyl, $C_1$–$C_4$alkylsulfinyl-$C_1$–$C_4$alkyl, $C_1$–$C_4$alkylsulfonyl-$C_1$–$C_4$alkyl, triazolyl, phenyl, phenylthio, phenylsulfinyl, phenylsulfonyl or phenoxy, wherein the phenyl-containing groups may be substituted by $C_1$–$C_3$alkyl, $C_1$–$C_3$haloalkyl, $C_1$–$C_3$alkoxy, $C_1$–$C_3$haloalkoxy, halogen, cyano or by nitro, and agronomically acceptable salts/N-oxides/isomers/enantiomers of such compounds.

The alkyl groups in the above substituent definitions may be straight-chain or branched and are, for example, methyl, ethyl, n-propyl, isopropyl, n-butyl, sec-butyl, isobutyl or tert-butyl. Alkoxy, alkenyl and alkynyl radicals are derived from the mentioned alkyl radicals. The alkenyl and alkynyl groups may be mono- or poly-unsaturated. Alkoxy is, for example, methoxy, ethoxy, propoxy, isopropoxy, n-butoxy, isobutoxy, sec-butoxy or tert-butoxy. Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl; preferably methoxycarbonyl or ethoxycarbonyl.

$M^+$ as an alkali metal ion, alkaline earth metal ion or ammonium ion is, for example, the sodium, potassium, calcium, magnesium, triethylammonium or diisopropylethylammonium cation.

Halogen is generally fluorine, chlorine, bromine or iodine. The same applies also to halogen in connection with other definitions, such as haloalkyl or halophenyl. Haloalkyl groups having a chain length of from 1 to 6 carbon atoms are, for example, fluoromethyl, difluoromethyl, chlorodifluoromethyl, trifluoromethyl, chloromethyl, dichloromethyl, trichloromethyl, 2,2,2-trifluoroethyl, 1-fluoroethyl, 2-fluoroethyl, 2-chloroethyl, 2-fluoroprop-2-yl, pentafluoroethyl, 1,1-difluoro-2,2,2-trichloroethyl, 2,2,3, 3-tetrafluoroethyl and 2,2,2-trichloroethyl, pentafluoroethyl, heptafluoro-n-propyl or perfluoro-n-hexyl.

Alkenyl and alkynyl groups may be mono- or polyunsaturated and also include alkyl, alkenyl or alkynyl chains having one or more double or triple bonds. Alkenyl is, for example, vinyl, allyl, isobuten-3-yl, $CH_2=CH-CH_2-CH=CH-$, $CH_2=CH-CH_2-CH_2-CH=CH-$ or $CH_3-CH=CH-CH_2-CH=CH-$. A preferred alkynyl is, for example, propargyl, and a preferred allenyl is $CH_2=C=CH_2-$.

An alkylene chain may also be substituted by one or more $C_1-C_3$alkyl groups, especially by methyl groups. Such alkylene chains and alkylene groups are preferably unsubstituted. The same applies also to all $C_3-C_6$cycloalkyl-, $C_3-C_5$oxacycloalkyl-, $C_3-C_5$thiacycloalkyl-, $C_3-C_4$dioxacycloalkyl-, $C_3-C_4$dithiacycloalkyl- or $C_3-C_4$oxathiacycloalkyl-containing groups, which, for example, may also occur as part of oxygen- and sulfur-containing heterocyclic ring systems of the radicals $Ra_1$ and $Ra_2$.

A $C_1-C_4$alkylene, $C_2-C_4$alkenylene or $C_2-C_4$alkynylene chain which may be interrupted by oxygen, $-N(C_1-C_4$alkyl)-, sulfur, sulfinyl or by sulfonyl, or in $X_2$ or $X_6$ denoting a $C_1-C_6$alkylene, $C_3-C_6$alkenylene or $C_3-C_6$alkynylene chain which may be mono- or polysubstituted by halogen or by $X_4$ or $X_8$, respectively, the unsaturated bonds of the chain not being bonded directly to the substituents $X_1$ and $X_5$, respectively, is to be understood as meaning, for example, $-CH_2-$, $-CH_2CH_2-$, $-CH_2CH_2CH_2-$, $-CH_2CH_2CH_2CH_2-$, $-CH(CH_3)-$, $-CH_2CH(CH_3)-$, $-CH_2CH(CH_3)CH_2-$, $-CH_2CH(O)CH_2-$, $-CH_2CH(OCH_3)CH_2-$, $-CH_2O-$, $-OCH_2-$, $-CH_2OCH_2-$, $-OCH_2CH_2-$, $-OCH_2CH_2CH_2-$, $-CH_2OCH_2CH_2-$, $-CH_2OCH(CH_3)CH_2-$, $-SCH_2-$, $-SCH_2CH_2-$, $-SCH_2CH_2CH_2-$, $-CH_2S-$, $-CH_2SCH_2-$, $-CH_2S(O)CH_2-$, $-CH_2SO_2CH_2-$, $-CH_2SCH_2CH_2-$, $-CH_2S(O)CH_2CH_2-$, $-CH_2SO_2CH_2CH_2-$, $-CH_2SO_2NH-$, $-CH_2N(CH_3)SO_2CH_2CH_2-$, $-N(SO_2Me)CH_2CH_2-$, $-CH_2C(O)NH-$ or $-CH_2NHC(O)CH_2-$. Accordingly, a $C_2-C_4$alkenylene chain which may optionally be interrupted by oxygen is to be understood as meaning, for example, $-CH=CH-CH_2-$, $-CH=CH-CH_2CH_2-$ or $-CH=CHCH_2OCH_2-$, and a $C_2-C_4$alkynylene chain which may optionally be interrupted by oxygen is to be understood as meaning, for example, $-C\equiv C-$, $-C\equiv CCH_2-$, $-C\equiv CCH_2O-$, $-C\equiv CCH_2OCH_2-$ or $-OC\equiv CCH_2-$.

A three- to ten-membered mono- or bi-cyclic ring system $Ra_1$ or $Ra_2$ which may be interrupted once or up to three times by substituents selected from oxygen, sulfur, S(O), $SO_2$, $N(Ra_6)$, carbonyl and $C(=NORa_7)$ and which is bonded to the carbon atom of the substituent $A_1$ or to the group $Q_1$ or $Q_2$, either directly or by way of a $C_1-C_4$alkylene, $C_2-C_4$alkenylene or $C_2-C_4$alkynylene bridge which may be interrupted by oxygen, $-N(C_1-C_4$alkyl)-, sulfur, sulfinyl or by sulfonyl, is to be understood as meaning, for example, 1-methyl-1H-pyrazol-3-yl, 1-ethyl-1H-pyrazol-3-yl, 1-propyl-1H-pyrazol-3-yl, 1H-pyrazol-3-yl, 1,5-dimethyl-1H-pyrazol-3-yl, 4-chloro-1-methyl-1H-pyrazol-3-yl, 1H-pyrazol-1-yl, 3-methyl-1H-pyrazol-1-yl, 3,5-dimethyl-1H-pyrazol-1-yl, 3-isoxazolyl, 5-methyl-3-isoxazolyl, 3-methyl-5-isoxazolyl, 5-isoxazolyl, 1H-pyrrol-2-yl, 1-methyl-1H-pyrrol-2-yl, 1H-pyrrol-1-yl, 1-methyl-1H-pyrrol-3-yl, 2-furanyl, 5-methyl-2-furanyl, 3-furanyl, 5-methyl-2-thienyl, 2-thienyl, 3-thienyl, 1-methyl-1H-imidazol-2-yl, 1H-imidazol-2-yl, 1-methyl-1H-imidazol-4-yl, 1-methyl-1H-imidazol-5-yl, 4-methyl-2-oxazolyl, 5-methyl-2-oxazolyl, 2-oxazolyl, 2-methyl-5-oxazolyl, 2-methyl-4-oxazolyl, 4-methyl-2-thiazolyl, 5-methyl-2-thiazolyl, 2-thiazolyl, 2-methyl-5-thiazolyl, 2-methyl-4-thiazolyl, 3-methyl-4-isothiazolyl, 3-methyl-5-isothiazolyl, 5-methyl-3-isothiazolyl, 1-methyl-1H-1,2,3-triazol-4-yl, 2-methyl-2H-1,2,3-triazol-4-yl, 4-methyl-2H-1, 2,3-triazol-2-yl, 1-methyl-1H-1,2,4-triazol-3-yl, 1,5-dimethyl-1H-1,2,4-triazol-3-yl, 3-methyl-1H-1,2,4-triazol-1-yl, 5-methyl-1H-1,2,4-triazol-1-yl, 4,5-dimethyl-4H-1,2, 4-triazol-3-yl, 4-methyl-4H-1,2,4-triazol-3-yl, 4H-1,2,4-triazol-4-yl, 5-methyl-1,2,3-oxadiazol-4-yl, 1,2,3-oxadiazol-4-yl, 3-methyl-1,2,4-oxadiazol-5-yl, 5-methyl-1, 2,4-oxadiazol-3-yl, 4-methyl-3-furazanyl, 3-furazanyl, 5-methyl-1,2,4-oxadiazol-2-yl, 5-methyl-1,2,3-thiadiazol-4-yl, 1,2,3-thiadiazol-4-yl, 3-methyl-1,2,4-thiadiazol-5-yl, 5-methyl-1,2,4-thiadiazol-3-yl, 4-methyl-1,2,5-thiadiazol-3-yl, 5-methyl-1,3,4-thiadiazol-2-yl, 1-methyl-1H-tetrazol-5-yl, 1H-tetrazol-5-yl, 5-methyl-1H-tetrazol-1-yl, 2-methyl-2H-tetrazol-5-yl, 2-ethyl-2H-tetrazol-5-yl, 5-methyl-2H-tetrazol-2-yl, 2H-tetrazol-2-yl, 2-pyridyl, 6-methyl-2-pyridyl, 4-pyridyl, 3-pyridyl, 6-methyl-3-pyridazinyl, 5-methyl-3-pyridazinyl, 3-pyridazinyl, 4,6-dimethyl-2-pyrimidinyl, 4-methyl-2-pyrimidinyl, 2-pyrimidinyl, 2-methyl-4-pyrimidinyl, 2-chloro-4-pyrimidinyl, 2,6-dimethyl-4-pyrimidinyl, 4-pyrimidinyl, 2-methyl-5-pyrimidinyl, 6-methyl-2-pyrazinyl, 2-pyrazinyl, 4,6-dimethyl-1,3,5-triazin-2-yl, 4,6-dichloro-1,3,5-triazin-2-yl, 1,3,5-triazin-2-yl, 4-methyl-1,3,5-triazin-2-yl, 3-methyl-1,2, 4-triazin-5-yl, 3-methyl-1,2,4-triazin-6-yl,

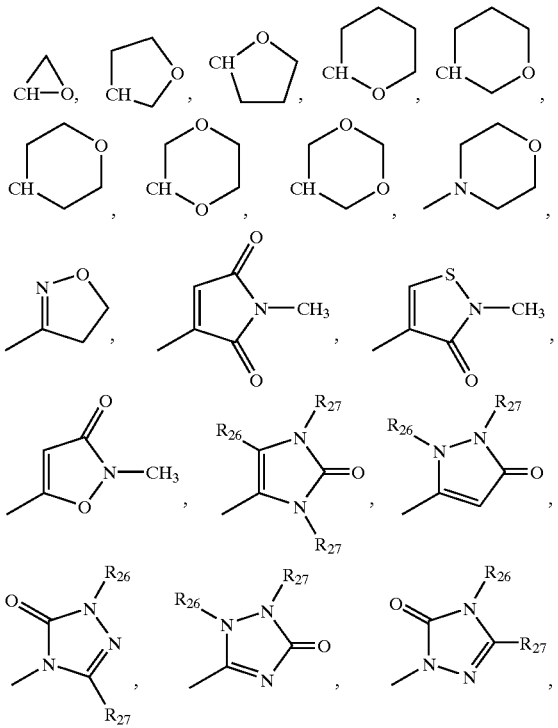

-continued

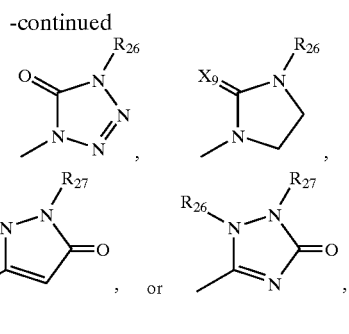

wherein each $R_{26}$ is methyl, each $R_{27}$, independently of any other, is hydrogen, $C_1$–$C_3$alkyl, $C_1$–$C_3$alkoxy, $C_1$–$C_3$alkylthio or trifluoromethyl, and $X_9$ is oxygen or sulfur.

A further fused, monocyclic or bicyclic ring system, which is formed, for example, by two adjacent substituents $Ra_1$ and $Ra_2$ or $Ra_1$ and $Ra_5$ and which is optionally interrupted once or up to three times by substituents selected from oxygen, sulfur, S(O), $SO_2$, —N($Ra_6$)—, carbonyl and C(=NO$Ra_7$), and which in addition may be substituted by one or more substituents, is to be understood as meaning, for example, a fused, bidentate ring system of formula

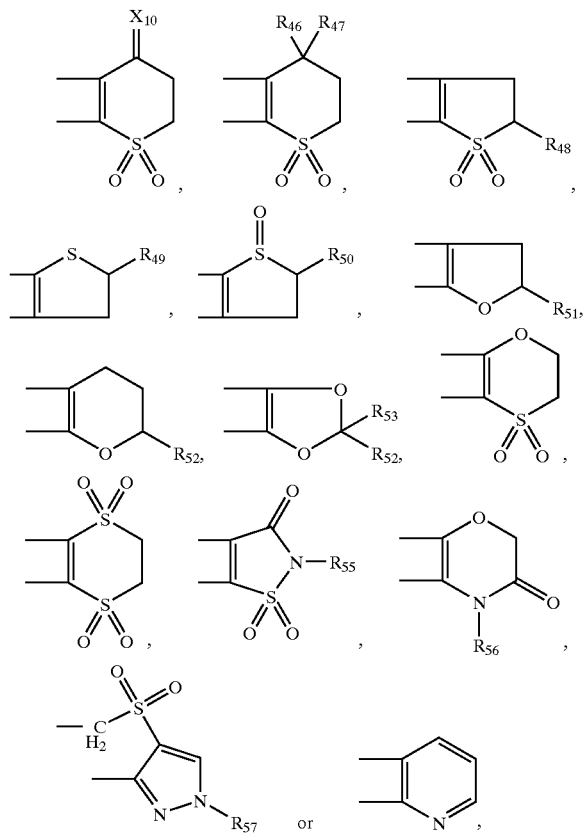

wherein, especially, $R_{46}$ is hydrogen, halogen, $C_1$–$C_4$alkyl, $C_1$–$C_4$haloalkyl, $C_1$–$C_4$alkoxy or $C_1$–$C_4$alkylthio; $R_{47}$ is hydrogen, halogen, $C_1$–$C_4$alkyl, $C_1$–$C_4$alkoxy; and $R_{50}$, $R_{51}$, $R_{52}$, $R_{53}$, $R_{54}$, $R_{55}$, $R_{56}$, $R_{57}$, $R_{58}$ and $R_{59}$ are hydrogen or $C_1$–$C_4$alkyl; and $X_{10}$ is oxygen or NO$R_{59}$.

A heteroaryl group Q substituted at least in the ortho position is to be understood as meaning especially a 5- or 6-membered aromatic heteroaryl group as listed above, which in addition is mono- to tri-substituted on the nitrogen atoms and/or carbon atoms by radicals selected from the definitions of $Ra_1$, $Ra_2$, $Ra_3$ or $Ra_4$ and $Ra_5$.

Especially advantageously, the cyclohexanedione herbicides described in WO/0015615, WO 00/37437, WO 01/66522 and WO 01/94339 may be prepared by the process according to the invention.

Compounds of formula I well suited to preparation according to the process of the invention are those wherein $R_1$ and $R_2$ are hydrogen;

A is unsubstituted $C_1$–$C_2$alkylene;

D and E together are unsubstituted $C_2$–$C_3$alkylene;

Q is $Q_1$, wherein $A_1$ is CR$a_1$ or N—(O)$_p$;

p is 0;

$Ra_1$ is hydrogen, $C_1$–$C_6$alkyl, hydroxy, $C_1$–$C_6$alkoxy, $C_1$–$C_6$haloalkoxy, $C_3$–$C_6$alkenyloxy, $C_3$–$C_6$haloalkenyloxy, $C_3$–$C_6$alkynyloxy, $C_1$–$C_4$alkoxy-$C_1$–$C_2$alkoxy, $C_1$–$C_4$alkoxy-$C_1$–$C_2$alkoxy-$C_1$–$C_2$alkoxy, ($C_3$–$C_6$cycloalkyl)-$C_1$–$C_2$alkoxy, (1,3-dioxolan-2-yl)-$C_1$–$C_2$alkoxy, (tetrahydrofuran-2-yl)-$C_1$–$C_2$alkoxy, (tetrahydrofuran-3-yl)oxy, (oxetan-3-yl)oxy, ($C_3$–$C_6$cycloalkyl)oxy, $C_1$–$C_4$alkylsulfonyloxy, $C_1$–$C_4$alkylthio, $C_1$–$C_4$alkylsulfonyl, $C_1$–$C_4$alkylamino, di($C_1$–$C_4$alkyl)amino, $C_1$–$C_2$alkoxyethylamino, $C_1$–$C_2$alkoxyethyl-(N-methyl)amino, morpholino, $C_1$–$C_4$alkylcarbonylamino-ethoxy, $C_1$–$C_4$alkoxycarbonyl, hydroxymethyl, $C_1$–$C_6$alkoxymethyl, $C_1$–$C_6$haloalkoxymethyl, $C_3$–$C_6$alkenyloxymethyl, $C_3$–$C_6$haloalkenyloxymethyl, $C_3$–$C_6$alkynyloxymethyl, $C_1$–$C_4$alkoxy-$C_1$–$C_2$alkoxymethyl, ($C_3$–$C_6$cycloalkyl)-methoxymethyl, (1,3-dioxolan-2-yl)-methoxymethyl, (tetrahydrofuran-2-yl)-methoxymethyl, (tetrahydrofuran-3-yl)oxymethyl, (oxetan-3-yl)oxymethyl, ($C_3$–$C_6$cycloalkyl)oxymethyl, $C_1$–$C_4$alkylcarbonylamino-$C_1$–$C_2$alkoxy, $C_1$–$C_4$haloalkyl, cyano, halogen, phenyl or benzyloxy, wherein a phenyl-containing group may itself be substituted by $C_1$–$C_3$alkyl, $C_1$–$C_3$haloalkyl, $C_1$–$C_3$alkoxy, $C_1$–$C_3$haloalkoxy, halogen, cyano or by nitro;

$Ra_2$ is $C_1$–$C_6$alkyl, $C_1$–$C_6$haloalkyl, $C_2$–$C_6$alkenyl, $C_2$–$C_6$haloalkenyl, $C_2$–$C_6$alkynyl, $C_3$–$C_6$cycloalkyl, halo- or $C_1$–$C_2$alkoxymethyl-substituted $C_3$–$C_6$cycloalkyl, $C_1$–$C_6$alkoxy, $C_3$–$C_6$alkenyloxy, $C_3$–$C_6$alkynyloxy, $C_1$–$C_6$haloalkoxy, $C_3$–$C_6$haloalkenyloxy, $C_1$–$C_4$alkoxy-$C_1$–$C_4$alkoxy, $C_1$–$C_4$alkylthio-$C_1$–$C_4$alkoxy, $C_1$–$C_4$alkylsulfinyl-$C_1$–$C_4$alkoxy, $C_1$–$C_4$alkylsulfonyl-$C_1$–$C_4$alkoxy, $C_1$–$C_4$alkoxycarbonyl-$C_1$–$C_4$alkoxy, $C_1$–$C_6$alkylthio, $C_1$–$C_6$alkylsulfinyl, $C_1$–$C_6$alkylsulfonyl, $C_1$–$C_6$haloalkylthio, $C_1$–$C_6$haloalkylsulfinyl, $C_1$–$C_6$haloalkylsulfonyl, $C_1$–$C_6$alkylaminosulfonyl, di($C_1$–$C_6$alkyl)aminosulfonyl, $C_1$–$C_4$alkylsulfonyloxy, $C_1$–$C_4$haloalkylsulfonyloxy, $C_1$–$C_4$alkylsulfonylamino, $C_1$–$C_4$alkylsulfonyl-N($C_1$–$C_4$alkyl), cyano, halogen, hydroxy-$C_1$–$C_4$alkyl, $C_1$–$C_4$alkoxy-$C_1$–$C_4$alkyl, $C_1$–$C_4$alkylthio-$C_1$–$C_4$alkyl, $C_1$–$C_4$alkylsulfinyl-$C_1$–$C_4$alkyl, $C_1$–$C_4$alkylsulfonyl-$C_1$–$C_4$alkyl, cyano-$C_1$–$C_4$alkyl, $C_1$–$C_6$alkylcarbonyloxy-$C_1$–$C_4$alkyl, $C_1$–$C_4$alkoxycarbonyl-$C_1$–$C_4$alkyl, $C_1$–$C_4$alkoxycarbonyloxy-$C_1$–$C_4$alkyl, phenoxy-$C_1$–$C_4$alkyl, benzyloxy-$C_1$–$C_4$alkyl, benzoyloxy-$C_1$–$C_4$alkyl, benzyloxy, benzylthio, phenoxy or phenylthio, wherein the phenyl-containing groups may themselves be substituted by $C_1$–$C_3$alkyl, $C_1$–$C_3$haloalkyl, $C_1$–$C_3$alkoxy, $C_1$–$C_3$haloalkoxy, halogen, cyano or by nitro; or Ra$_2$ is the group —X$_1$—X$_3$ or the group —X$_2$—X$_1$—X$_3$, wherein X$_1$, X$_2$ and X$_3$ are as defined hereinabove;

Ra$_3$ is hydrogen;

Ra$_4$ is hydrogen or methyl;

Ra$_5$ is C$_1$–C$_6$haloalkyl, C$_2$–C$_6$haloalkenyl, C$_1$–C$_6$alkoxy, C$_1$–C$_6$haloalkoxy, C$_1$–C$_6$alkylthio, C$_1$–C$_6$alkylsulfinyl, C$_1$–C$_6$alkylsulfonyl, C$_1$–C$_6$haloalkylthio, C$_1$–C$_6$haloalkylsulfinyl, C$_1$–C$_6$haloalkylsulfonyl, C$_1$–C$_6$alkylsulfonyloxy, C$_1$–C$_4$alkylaminosulfonyl, di(C$_1$–C$_4$alkyl)aminosulfonyl, C$_1$–C$_4$alkylsulfonylamino, C$_1$–C$_4$alkylsulfonyl-N(C$_1$–C$_4$alkyl)-, cyano, halogen, C$_1$–C$_4$alkoxymethyl, C$_1$–C$_4$alkylthiomethyl, C$_1$–C$_4$alkylsulfinylmethyl, C$_1$–C$_4$alkylsulfonylmethyl or 1H-1,2,4-triazol-1-yl.

Compounds of formula I especially well suited to preparation according to the process of the invention are those wherein R$_1$ and R$_2$ are hydrogen, A is methylene, D and E together are ethylene, Q is Q$_1$, wherein A$_1$ is nitrogen, Ra$_3$ and Ra$_4$ are hydrogen, Ra$_5$ is C$_1$–C$_3$haloalkyl, preferably trifluoromethyl, difluorochloromethyl or difluoromethyl, especially trifluoromethyl, and Ra$_2$ is C$_1$–C$_4$alkyl, C$_1$–C$_4$haloalkyl, C$_1$–C$_4$alkoxy-C$_1$–C$_4$alkyl or C$_1$–C$_4$alkoxy-C$_1$–C$_2$alkoxy-C$_1$–C$_2$alkyl, preferably methyl, ethyl, methoxymethyl, ethoxymethyl, methoxypropyl or methoxyethoxymethyl, especially methoxyethoxymethyl.

Compounds of formula I very especially well suited to preparation according to the process of the invention are those wherein R$_1$ and R$_2$ are hydrogen, A is methylene, D and E together are ethylene, Q is Q$_1$, wherein A$_1$ is nitrogen, Ra$_3$ and Ra$_4$ are hydrogen, Ra$_5$ is trifluoromethyl and Ra$_2$ is C$_1$–C$_4$alkoxy-C$_1$–C$_2$alkoxy-C$_1$–C$_2$alkyl, especially preferably methoxyethoxymethyl.

A special advantage of the process according to the invention is that the starting compounds of formula II are readily obtainable. When D and E together are other than C$_2$–C$_3$alkylene, those starting compounds are either known, for example from J. Gen. Chem. USSR, 1964, 34, 3509 (engl. Transl. 1964, 34, 3553); Tetrahedron Letters, 1984, 25, 3179; J.A.C.S. 1987, 109, 6385; Journal of Organic Chemistry, 1988, 53, 4923 or Arm. Khim. Zh, 1976, 29, 342, or can be prepared according to the methods described therein; or, especially when D together with E forms a C$_2$–C$_3$alkylene chain, can be obtained by oxidation of a compound of formula VI:

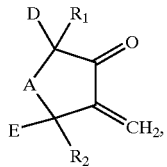

(VI)

wherein R$_1$, R$_2$, A, D and E are as defined for formula I, the resulting compounds of formula II generally not requiring isolation for use in the process according to the invention and being usable directly from the reaction mixture. The compounds of formula VI are known or are obtainable according to known methods, for example by addition of formaldehyde with removal of water. The preparation of the compound of formula VI wherein R$_1$ and R$_2$ are hydrogen, A is methylene and D and E together are ethylene (methylene-norcamphor) is described, for example, in JP-10-265415.

Oxidising agents suitable for the conversion of compounds of formula VI to compounds of formula II are organic peracids, such as peracetic acid, trifluoroperacetic acid, performic acid, perpropionic acid, perbenzoic acid, m-chloroperbenzoic acid or monoperoxyphthalic acid, hydrogen peroxide or hydrogen peroxide in the presence of catalytic amounts of selenium dioxide, where appropriate in the presence of an additional amount of base in an inert solvent at temperatures of from −20° C. to 50° C. Suitable bases include, for example, sodium acetate, potassium acetate, sodium carbonate, sodium hydrogen carbonate, potassium carbonate, calcium carbonate, barium oxide, potassium hydrogen phosphate and potassium dihydrogen phosphate. Suitable solvents include, for example, dichloromethane, dichloroethane, acetic acid, acetic anhydride and mixtures thereof, e.g. dichloromethane and acetic acid or acetic acid and acetic anhydride.

The alkali metal and alkaline earth metal alcoholates may be used in catalytic or stoichiometric amounts in the conversion of a compound of formula II to a salt of formula III. When catalytic amounts are used it is necessary to add a further base. The further base may be added in stoichiometric amounts or in excess. It is more advantageously used in stoichiometric amount up to a slight excess. As additional bases there may used, for example, inorganic bases, such as carbonates, for example potassium carbonate, oxides, for example barium oxide, and hydrides, for example sodium hydride. Catalytic amounts of alkali metal and alkaline earth metal alcoholates are to be understood as being from 0.0001% to 25%, preferably from 0.1% to 10%.

In a preferred embodiment of the process according to the invention, the alcoholates of alkali metals and alkaline earth metals, especially those of lithium, sodium and potassium, are used without an additional base, in stoichiometric amounts or in excess, but especially preferably in stoichiometric amounts.

Preferred alkali metal and alkaline earth metal alcoholates are those of lithium, sodium and potassium, especially the methanolates and ethanolates. Alkali metal and alkaline earth metal alcoholates that are especially preferred are sodium methanolate, sodium ethanolate, sodium isopropanolate, sodium n-butanolate, potassium tert-butanolate, sodium n-pentanolate, sodium tert-amylate and sodium 2-methoxyethanolate; sodium methanolate is more especially preferred.

The conversion is carried out preferably in the presence of a solvent or especially in the presence of a solvent mixture. Suitable solvents are toluene, xylene, chlorobenzene, methylnaphthalene, or alcohols such as methanol, ethanol, isopropanol, amyl alcohol, or tetrahydrofuran or dioxane, or aprotic solvents such as propionitrile, dimethylformamide, N-methylpyrrolidone or dimethyl sulfoxide, or 2-methyl-5-ethylpyridine or the like, or mixtures of such solvents, for example toluene and dimethylformamide or toluene and N-methyl-pyrrolidone.

In reaction step a), special preference is given to the use of toluene and, as additional solvent, dimethylformamide or N-methylpyrrolidone, since then the compounds of formula III can especially advantageously be precipitated from the reaction mixture and consequently further base-catalysed secondary reactions are substantially avoided.

In reaction step a), the solvent or solvent mixture is used in an amount at which the salt of formula III, preferably the sodium salt, is precipitated in readily crystallisable form from the reaction medium and the reaction mixture nevertheless remains readily stirrable. In the conversion of compounds of formula II to compounds of formula III wherein M$^+$ is an alkali metal cation, preferably the sodium cation, especially solvent mixtures of toluene and from 1 to 15% dimethylformamide or from 1 to 15% N-methylpyrrolidone are advantageous, special preference being given to a mixture of from 3 to 8% dimethylformamide in toluene.

Depending on the solvent, the conversions are carried out at temperatures of approximately from 0° C. to the boiling temperature and advantageously under anhydrous conditions. In an especially advantageous embodiment of the process according to the invention, the conversion is carried out in toluene, using sodium methanolate as the base, at a temperature of from 80° C. to the boiling temperature, during which the methanol released is continuously distilled off in order to avoid secondary reactions.

Especially, sodium methanolate in the form of an approximately 30% methanolic solution in a mixture of toluene and approximately from 1 to 15% dimethylformamide can be used as initial charge, with the result that, on heating, first of all the methanol is distilled off up to a column head temperature of approximately from 105 to 110° C., and only then is the compound of formula II, dissolved in a small amount of toluene, added dropwise in such a manner that the methanol released is continuously removed from the reaction mixture by further distillation and hence the salt of formula III is able to precipitate from the reaction mixture in the form of a pure, readily stirrable crystallisate.

It is advantageous that, when the conversion is carried out using alcoholate anions as catalyst, also the corresponding alcoholate-forming cation is used as the base for the precipitation of the enolate of formula I. Suitable amounts of alkali metal alcoholate are from 1.0 up to 2.5 equivalents, especially from 1.0 up to approximately 1.5 equivalents. Special preference is given to from 1.0001 to 1.1 equivalents of sodium methanolate as the base.

In a further embodiment of the process according to the invention, in reaction step a) catalytic amounts of cyanide ions are used in the presence of an additional amine base. Suitable bases are especially tertiary amines, such as trialkylamines, e.g. trimethylamine, triethylamine, diisopropylethylamine (Hünig's base), tri-n-butylamine, N,N-dimethylaniline and N-methylmorpholine. As a source of cyanide ions there are preferably used the alkali metal cyanides, e.g. sodium cyanide or potassium cyanide, or copper(I) cyanide, or organic cyanohydrins, such as acetone cyanohydrin, or trialkylsilyl cyanides, such as trimethylsilyl cyanide, or tertiary ammonium bases, such as tetraethylammonium cyanide. In that process variant according to the invention, the amount of alkali metal cyanide used ranges from a small amount up to a slight excess. The cyanides are used in amounts of from 0.1% up to approximately 25%, preferably from 1% to approximately 15%, in the presence of an additional base, such as especially triethylamine or Hünig's base, the amount of base being from 1 to 6 equivalents, especially from 1.1 to approximately 2.5 equivalents.

That embodiment of the process according to the invention is preferably carried out in an inert solvent, such as n-heptane, toluene, xylene, dichloromethane, dichloroethane, dimethoxyethane, tetrahydrofuran, dioxane, tert-butyl methyl ether, ethyl acetate, acetone, 2-butanone, acetonitrile, propionitrile, dimethylformamide or N-methylpyrrolidone at temperatures of from −5° C. to approximately 80° C., especially preferably in acetonitrile or dichloromethane at temperatures of from approximately 10° C. to approximately 60° C.

Depending on the solvents employed, additives such as, for example, lithium chloride, lithium bromide, or phase transfer catalysts, such as, for example, tetrabutylammonium bromide or especially tetraethylammonium cyanide, may optionally be used for such reactions, or drying agents, such as magnesium sulfate or molecular sieves, may optionally be used, but such additives are generally not required.

Reaction Step b):

The compound of formula III obtained in reaction step a) is preferably reacted directly, without isolation of intermediates, with the compound of formula IV. That reaction procedure is a special advantage of the process according to the invention The reaction mixture obtained in reaction step a) is cooled to a temperature of from 10° C. to 50° C. and the compound of formula IV, optionally dissolved in a solvent or solvent mixture, for example toluene, tetrahydrofuran or acetonitrile, is added thereto. The compound of formula V can then be isolated according to conventional working-up procedures by extraction with an organic solvent and washing with dilute alkaline solution at a pH of from 7 to 9.

In a preferred embodiment of the process according to the invention, in reaction step a) sodium methanolate is used as the base, preferably in an amount of from 1 to 1.5 equivalents, especially preferably from 1.0001 to 1.1 equivalents, and the compound of formula IV is added in an amount ranging from stoichiometric up to a slight excess of from 1.0001 to 1.1 equivalents. The leaving group X in that embodiment is especially fluorine, chlorine, bromine, triazolyl, imidazolyl or cyano, more especially chlorine.

The compounds of formula IV are either known or can be prepared according to methods known to the person skilled in the art. Compounds of formula IV and the preparation thereof are described, for example, in WO/0015615, WO 00/37437, WO 01/66522 and WO 01/94339.

Reaction Step c):

In an especially preferred embodiment of the process according to the invention, the reaction according to reaction step c) is carried out without the isolation of intermediates, that is, the compound of formula V obtained according to reaction step b) is treated in situ with cyanide ions in the presence of a base.

The cyanide ions are preferably used in amounts of from 0.01% to 15%. As soon as after the beginning of the reaction, preferably at a temperature of approximately 20° C., the intermediate of formula V that is formed is detectable, for example by means of thin-layer chromatography, the reaction can be brought to an end by adding further catalytic amounts of cyanide ions and, where appropriate, an additional amount of base, for example from 0.1 to 2.5 equivalents of triethylamine, or Hünig's base, and the compounds of formula I can be isolated and purified according to conventional working-up methods (e.g. by washing and extraction procedures and by crystallisation). A suitable source of cyanide ions is, for example, sodium cyanide, potassium cyanide, copper(I) cyanide, acetone cyanohydrin or trimethylsilyl cyanide, preferably potassium cyanide. Such enol ester rearrangements are described, for example, in EP-A-0 186 117.

In a very especially preferred embodiment of the process according to the invention, reaction steps a), b) and c) are carried out as a one-pot reaction, without isolation of intermediates.

In a further, likewise preferred embodiment of the process according to the invention, reaction steps a) and b) are carried out as a one-pot reaction and, in an additional washing and purification process, the neutral intermediate of formula IV is first of all freed of impurities and then transferred directly to reaction step c) (industrial cascade reaction).

The process according to the invention is illustrated in the following Preparation Examples:

EXAMPLE P1

Preparation of the triethylammonium salt of 4-hydroxybicyclo[3.2.1]oct-3-en-2-one from 4-methylene-3-oxabicyclo[3.2.1]octan-2-one

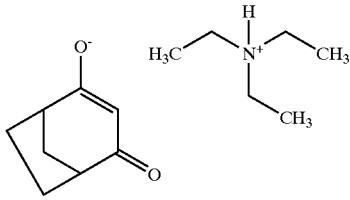

2.76 g (20 mmol) of 4-methylene-3-oxabicyclo[3.2.1]octan-2-one are heated at a temperature of 55° C. for 2.5 hours in the presence of 2.23 g (20 mmol) of triethylamine and 0.13 g (2 mmol) of potassium cyanide in 20 ml of acetonitrile. The turbid reaction mixture is filtered over Hyflo® and evaporated to dryness. The triethylammonium salt of 4-hydroxybicyclo[3.2.1]oct-3-en-2-one is obtained in the form of a resinous, hygroscopic product.

EXAMPLE P2

Preparation of the ethyldiisopropylammonium salt of 4-hydroxybicyclo[3.2.1]oct-3-en-2-one from 4-methylene-3-oxabicyclo[3.2.1]octan-2-one

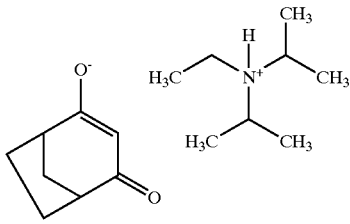

Analogously to Example P1, 1.38 g (10 mmol) of 4-methylene-3-oxabicyclo[3.2.1]octan-2-one are stirred over a period of 12 hours in the presence of 1.29 g (10 mmol) of Hünig's base and 0.13 g of potassium cyanide in 10 ml of acetonitrile. Solid components (potassium salts) are filtered off and the filtrate is evaporated to dryness to yield the ethyldiisopropyl-ammonium salt of 4-hydroxybicyclo[3.2.1]oct-3-en-2-one in the form of a resin.

EXAMPLE P3

Preparation of the sodium salt of 4-hydroxybicyclo[3.2.1]oct-3-en-2-one

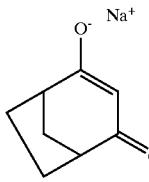

At a temperature of 110° C., a 30% solution of 12.1 g (0.22 mol) of sodium methanolate in methanol is added dropwise to a solution of 190 ml of toluene and 10 ml of dimethylformamide, during the course of which the methanol is continuously removed by distillation. There are added dropwise to the resulting suspension over a period of 30 minutes, with further removal of methanol by distillation, 20.7 g (0.15 mol) of 4-methylene-3-oxa-bicyclo[3.2.1]octan-2-one dissolved in 20 ml of toluene. After stirring for a further 2 hours at boiling temperature, the reaction mixture is allowed to cool and the precipitated product is filtered off and washed with toluene.

EXAMPLE P4

2-Methoxy-4-methylsulfanylbenzoic acid 4-oxobicyclo[3.2.1]oct-2-en-2-yl-2-one ester from 4-methylene-3-oxabicyclo[3.2.1]octan-2-one

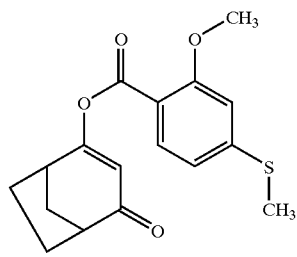

1.38 g (0.01 mol) of 4-methylene-3-oxabicyclo[3.2.1]octan-2-one are stirred for 12 hours in the presence of 1.29 g (0.01 mol) of Hünig's base and 0.13 g of potassium cyanide in 10 ml of acetonitrile. Solid components precipitated from the reaction mixture are then filtered off. While controlling the temperature, 1.73 g (8 mmol) of solid 2-methoxy-4-methylsulfanylbenzoyl chloride (m.p. 72–72.5° C.), freshly prepared with thionyl chloride from 2-methoxy-4-methylsulfanylbenzoic acid, are then introduced at a temperature of 20° C. After stirring for 30 minutes, extraction with ethyl acetate against water and concentration by evaporation are carried out. The residue (3.12 g) is purified by means of column chromatography (eluant: ethyl acetate/hexane 1:3). 1.78 g of 2-methoxy-4-methylsulfanyl-benzoic acid 4-oxobicyclo[3.2.1]oct-2-en-2-yl-2-one ester are obtained in the form of a resinous product (yield: 55.9% based on the 4-methylene-3-oxabicyclo[3.2.1]octan-2-one used or 69.9% based on the 2-methoxy-4-methylsulfanylbenzoyl chloride used). $^1$H-NMR (CDCl$_3$): 7.46 ppm, d, 1H; 6.83 ppm, d, 1H; 6.82 ppm, s, 1H; 5.68 ppm, s, 1H; 3.93 ppm, s, 3H; 3.04 ppm, m, 1H; 2.96 ppm, m, 1H; 2.52 ppm, s, 3H; 2.0–2.3 ppm, 4H; 1.7 ppm, 2H.

EXAMPLE P5

Preparation of 4-hydroxy-3-(2-methoxy-4-methylsulfanylbenzoyl)-bicyclo[3.2.1]oct-3-en-2-one

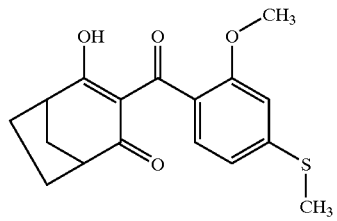

The compound prepared according to Example P4 is treated in the presence of 2 equivalents of triethylamine with a catalytic amount of acetone cyanohydrin in acetonitrile at a temperature of 20° C. 4-Hydroxy-3-(2-methoxy-4-methylsulfanylbenzoyl)-bicyclo[3.2.1]-oct-3-en-2-one (compound of formula I wherein Q is 2-methoxy-4-methylthiobenzoyl) is obtained. $^1$H-NMR (CDCl$_3$): 17.18 ppm, s, OH; 7.24 ppm, d, 1H; 6.84 ppm, d, 1H; 6.73, s, 1H; 3.73, s, 3H; 3.1 ppm, m, 1 H; 2.9 ppm, m, 1H; 2.50 ppm, s, 3H; 1.6–2.3 ppm, 6H.

EXAMPLE P6

4-Methanesulfonyl-2-nitrobenzoic Acid 4-oxobicyclo[3.2.1]oct-2-en-2-yl ester (Known from U.S. Pat. No. 5,608,101) from 4-methylene-3-oxabicyclo[3.2.1]octan-2-one

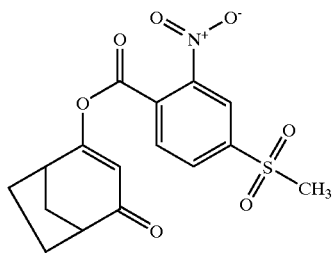

1.38 g (0.01 mol) of 4-methylene-3-oxabicyclo[3.2.1]octan-2-one are stirred for 12 hours at a temperature of 20° C. in the presence of 1.11 g (0.01 mol) of triethylamine and 65 mg (1 mmol) of potassium cyanide in 20 ml of acetonitrile, the 4-hydroxybicyclo[3.2.1]oct-3-en-2-one triethylammonium salt formed partially crystallising out. While controlling the temperature, 2.64 g (0.01 mol) of freshly prepared 4-methanesulfonyl-2-nitrobenzoyl chloride are introduced into the resulting suspension at a temperature of 20° C. After stirring for 30 minutes at a temperature of 20° C., extraction is carried out with ethyl acetate against 5% sodium hydrogen carbonate solution, followed by washing once with dilute hydrochloric acid and once with water and evaporating to dryness. The residue (3.2 g) is filtered through a small amount of silica gel (eluant: ethyl acetate/hexane 1:1), yielding 4-methanesulfonyl-2-nitrobenzoic acid 4-oxobicyclo[3.2.1]oct-2-en-2-yl ester in form of a viscous oil: yield: 2.48 g (67.9%); $^1$H-NMR (CDCl$_3$): 8.84 ppm, s, 1H; 8.34 ppm, d, 1H; 8.03 ppm, d, 1H; 5.90 ppm, s, 1H; 3.17 ppm, s, 3H; 3.0–3.15 ppm, 2H; 1.6–2.3 ppm, 6H.

EXAMPLE P7

Preparation of 4-hydroxy-3-(4-methanesulfonyl-2-nitrobenzoyl)-bicyclo[3.2.1]oct-3-en-2-one (Known From U.S. Pat. No. 5,801,120)

2.48 g of the compound prepared according to Example P6 are treated for 1 hour at a temperature of 20° C., in the presence of one equivalent of triethylamine, with a catalytic amount of potassium cyanide (10 mol %) in acetonitrile. 4-Hydroxy-3-(4-methanesulfonyl-2-nitrobenzoyl)-bicyclo[3.2.1]oct-3-en-2-one (compound of formula I wherein Q is 2-nitro-4-methanesulfonyl) is obtained. Yield: 1.41 g, or 56.8% based on the 4-hydroxybicyclo-[3.2.1]oct-3-en-2-one used.

EXAMPLE P8

4-Hydroxy-3-(4-methanesulfonyl-2-nitrobenzoyl)-bicyclo[3.2.1]oct-3-en-2-one from 4-methylene-3-oxabicyclo[3.2.1]octan-2-one

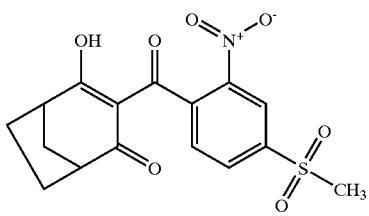

a) 2.76 g (0.02 mol) of 93% 4-methylene-3-oxabicyclo[3.2.1]octan-2-one and 4.45 g (0.044 mmol) of triethylamine are stirred for 7 hours at room temperature in 50 ml of acetonitrile in the presence of 130 mg (2 mmol) of potassium cyanide. 4.22 g (0.16 mol) of freshly prepared 4-methanesulfonyl-2-nitrobenzoyl chloride are then introduced and stirring is carried out for 12 hours at a temperature of 20° C. If, according to monitoring by thin-layer chromatography, relatively large amounts of the intermediate 4-methanesulfonyl-2-nitro-benzoic acid 4-oxobicyclo[3.2.1]oct-2-en-2-yl ester (known from U.S. Pat. No. 5,801,120) are still detectable, then a further 130 mg (2 mmol) of potassium cyanide are added and stirring is continued for a further 2 hours until conversion is complete. The reaction mixture is then taken up in ethyl acetate and extracted at a pH value of 13 against water. The aqueous phase is then acidified using hydrochloric acid and extracted at a pH value of approximately 4 using fresh ethyl acetate, dried over Na$_2$SO$_4$ and concentrated to a slight extent. The product, dissolved in warm ethyl acetate, is treated with activated carbon and filtered off with suction (suction filter) through a small amount of silica gel, then concentrated further and caused to crystallise by adding a small amount of hexane. 1.69 g of pure 4-hydroxy-3-(4-methanesulfonyl-2-nitrobenzoyl)-bicyclo[3.2.1]oct-3-en-2-one having a melting point of 170–170.5° C. are obtained. Further product (1.65 g) can be obtained from the mother liquor by recrystallisation. Total yield: 3.34 g, or 49.1% based on the starting material 4-methylene-3-oxabicyclo[3.2.1]octan-2-one used or 57.1% based on the starting material 4-methanesulfonyl-2-nitrobenzoic acid used. $^1$H-NMR (CDCl$_3$): 15.94 ppm, s, 1H; 8.74, s, 1H; 8.24 ppm, d, 1H; 7.48 ppm, d, 1H; 3.20 ppm, m, 1H; 3.19 ppm, s, 3H; 2.84 ppm, m, 1H; 2.0–2.3 ppm, 4H; 1.6–1.8 ppm, 2H.

b) 2.76 g (0.02 mol) of 93% 4-methylene-3-oxabicyclo[3.2.1]octan-2-one and 4.45 g (0.044 mmol) of triethylamine are stirred for 6 hours at a temperature of 20° C. in 50 ml of acetonitrile in the presence of 170 mg (2 mmol) of acetone cyanohydrin. 4.22 g (0.16 mol) of 4-methanesulfonyl-2-nitrobenzoyl chloride are then introduced and stirring is continued for a further 12 hours at a temperature of 20° C. A further 170 mg (2 mmol) of acetone cyano-hydrin are then added and stirring is continued for a further 30 minutes until conversion is complete. The reaction mixture is then taken up in ethyl acetate and extracted at a pH value of 13 against water. The aqueous phase is acidifed and extracted with fresh ethyl acetate, once at pH 5 and once at pH 4, dried and concentrated by evaporation. 3.05 g of 4-hydroxy-3-(4-methanesulfonyl-2-nitrobenzoyl)-bicyclo[3.2.1]oct-3-en-2-one with a good level of purity are obtained. The yield is 44.9% based on the starting material 4-methylene-3-oxabicyclo[3.2.1]octan-2-one or 52.2% based on the starting material 4-methanesulfonyl-2-nitrobenzoic acid.

EXAMPLE P9

Preparation of 4-hydroxy-3-(2-methyl-6-trifluoromethylpyridine-3-carbonyl)-bicyclo[3.2.1]oct-3-en-2-one (known from WO 00/15615) from 4-methylene-3-oxa-bicyclo[3.2.1]octan-2-one

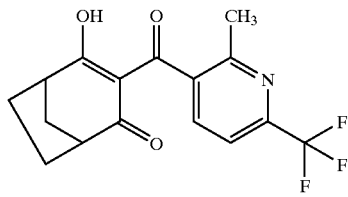

2.07 g (0.015 mol) of distilled 4-methylene-3-oxabicyclo[3.2.1]octan-2-one and 3.34 g (0.033 mol) of triethylamine are stirred for 2.5 hours at a temperature of 60° C. in 50 ml of acetonitrile in the presence of 98 mg (1.5 mmol) of potassium cyanide. Cooling to a temperature of 20° C. is then carried out and 2.35 g (0.11 mol) of 2-methyl-6-trifluoromethyl-nicotinoyl chloride, freshly prepared according to WO 00/15615, dissolved in a small amount of acetonitrile are added. The 2-methyl-6-trifluoromethylnicotinic acid 4-oxobicyclo[3.2.1]oct-2-en-2-yl ester (known from WO 00/15615) obtained in situ as intermediate is fully converted within a period of 3.5 hours (monitoring by thin-layer chromatography). The reaction mixture is then acidified with dilute hydrochloric acid and extracted with ethyl acetate against water at a pH value of 2, dried over $Na_2SO_4$ and concentrated by evaporation. The product is purified by means of column chromatography (eluant: ethyl acetate/hexane 4:1) to yield 3.16 g of 90% 4-hydroxy-3-(2-methyl-6-trifluoromethylpyridine-3-carbonyl)-bicyclo[3.2.1]oct-3-en-2-one (58.3% based on the 4-methylene-3-oxabicyclo[3.2.1]octan-2-one used or 83.3% based on the 2-methyl-6-trifluoromethylnicotinoyl chloride used).

[1] H-NMR (CDCl$_3$): 17.2 ppm, s, 1H; 7.48 ppm, m, 2H; 3.2 ppm, m, 1H; 2.9 ppm, m, 1H; 2.47 ppm, s, 3H; 1.4–1.7 ppm, 6H.

EXAMPLE P10

4-Hydroxy-3-(2-methyl-7-methylsulfanylbenzofuran-4-carbonyl)-bicyclo[3.2.1]oct-3-en-2-one from 4-methylene-3-oxabicyclo[3.2.1]octan-2-one

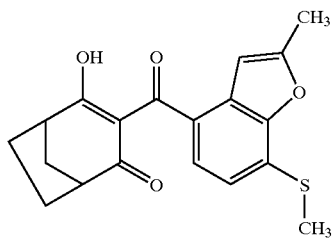

1.01 g (7.3 mmol) of 4-methylene-3-oxabicyclo[3.2.1]octan-2-one and 1.52 g (15 mmol) of triethylamine in 50 ml of acetonitrile are stirred for 7 hours at a temperature of 20° C. in the presence of 48 mg (0.7 mmol) of potassium cyanide. 1.75 g (7.3 mmol) of 2-methyl-7-methylsulfanylbenzofuran-4-carbonyl chloride (m.p. 123.5–124° C.) freshly prepared with oxalyl chloride from 2-methyl-7-methylsulfanylbenzofuran-4-carboxylic acid (m.p. 235–235.5° C.) are then added and stirring is carried out for 12 hours. If, after monitoring by thin-layer chromatography, relatively large amounts of the intermediate 2-methyl-7-methylsulfanylbenzofuran-4-carboxylic acid 4-oxobicyclo[3.2.1]oct-2-en-2-yl ester formed in situ are still detectable, then for complete conversion of that compound a further 3 drops of acetone cyanohydrin are added and the mixture is stirred again for 1.5 hours at a temperature of 40° C. The mixture is then diluted with ethyl acetate and extracted with water at pH 9. The aqueous phase is extracted with fresh ethyl acetate, once at pH 6 and once at pH 4, and concentrated by evaporation after combining the phases. 1.27 g (90.8%) of 4-hydroxy-3-(2-methyl-7-methylsulfanylbenzofuran-4-carbonyl)-bicyclo[3.2.1]oct-3-en-2-one ($^1$H-NMR (CDCl$_3$): 7.48 ppm, d, 1H; 7.02 ppm, d, 1H; 6.52 ppm, s, 1H; 3.05 ppm, b, 2H; 2.64 ppm, s, 3H; 2.48 ppm, s, 3H; 1.6–2.3 ppm, 6H) are obtained in the form of a resinous product.

That product can, if desired, be reacted directly in the subsequent oxidation stage, for example with sodium iodate in methanol, to form 4-hydroxy-3-(7-methanesulfinyl-2-methylbenzofuran-4-carbonyl)-bicyclo[3.2.1]oct-3-en-2-one (m.p.: 243–243.5° C.).

EXAMPLE P11

Preparation of 4-hydroxy-3-(7-methanesulfonyl-2-methylbenzofuran-4-carbonyl)-bicyclo[3.2.1]oct-3-en-2-one from 4-methylene-3-oxabicyclo[3.2.1]octan-2-one

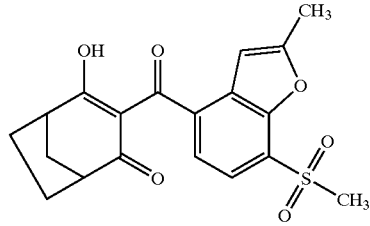

530 mg of technical grade 4-hydroxy-3-(7-methanesulfonyl-2-methylbenzofuran-4-carbonyl)-bicyclo[3.2.1]oct-3-en-2-one are prepared analogously to Example P10, in a one-pot process without isolation of intermediates, from 200 mg (1.5 mmol) of 4-methylene-3-oxabicyclo[3.2.1]octan-2-one in 50 ml of acetonitrile in the presence of 304 mg (3 mmol) of triethylamine, 10 mg (0.15 mmol) of potassium cyanide and 410 mg (1.5 mmol) of 2-methyl-7-methylsulfanylbenzofuran-4-carbonyl chloride (m.p. 145.5–146° C.) freshly prepared with oxalyl chloride from 2-methyl-7-methylsulfanyl-benzofuran-4-carboxylic acid (m.p. 228–228.5° C.), the product being isolated from the aqueous phase at pH 2 using ethyl acetate. After chromatographic purification using ethyl acetate and methanol, 9:1, 410 mg (75.5% based on 4-methylene-3-oxabicyclo[3.2.1]octan-2-one) of pure 4-hydroxy-3-(7-methanesulfonyl-2-methylbenzofuran-4-carbonyl)-bicyclo[3.2.1]oct-3-en-2-one having a melting point of 258.5–259° C. are obtained; $^1$H-NMR (CDCl$_3$): 17.08 ppm, s, OH; 7.78 ppm, d, 1 H; 7.39 ppm, d, 1H; 6.49 ppm, s, 1H; 3.32 ppm, s, 3H; 3.2 ppm, m, 1H; 2.96 ppm, m, 1H; 2.53 ppm, s, 3H; 1.6–2.3 ppm, 6H.

EXAMPLE P12

Preparation of 3-cyclopropanecarbonyl-4-hydroxybicyclo[3.2.1]oct-3-en-2-one from 4-methylene-3-oxabicyclo[3.2.1]octan-2-one

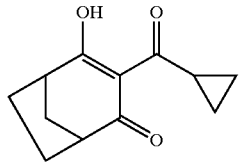

Analogously to Example P10, there are prepared from 829 mg (6 mmol) of 4-methylene-3-oxabicyclo[3.2.1]octan-2-one, 1.2 g (12 mmol) of triethylamine in 15 ml of acetonitrile in the presence of 39 mg (0.6 mmol) of potassium cyanide and 627 mg (6 mmol) of cyclopropanecarboxylic acid chloride, in a one-pot process without isolation of intermediates, 1.12 g (90.5%) of technical grade 3-cyclopropanecarbonyl-4-hydroxybicyclo[3.2.1]oct-3-en-2-one which, recrystallised from ethyl acetate/hexane, melts at a temperature of 71.5–72° C.;

$^1$H-NMR (CDCl$_3$): 18.33 ppm, s, OH; 3.61 ppm, m, 1H; 2.99 ppm, m, 2H; 1.5–2.2 ppm, 6H; 1.1–1.3 ppm, 4H.

EXAMPLE P13

2,3-Dichloro-4-methanesulfonylbenzoic Acid 4-oxobicyclo[3.2.1]oct-2-en-2-yl ester (known from U.S. Pat. No. 5,801,120) from 4-methylene-3-oxabicyclo[3.2.1]octan-2-one

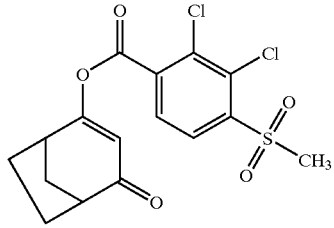

3.6 g of a 30% sodium methanolate solution (0.022 mol) are heated to a column head temperature of 108° C. in a mixture of 19 ml of toluene and 1 ml of dimethylformamide, methanol being removed by distillation. With removal of methanol by distillation being continued, 2.76 g (0.02 mol) of 4-methylene-3-oxabicyclo[3.2.1]octan-2-one dissolved in 3 ml of toluene are then added dropwise. After stirring for one hour, the mixture is cooled to a temperature of 20° C. and, while controlling the temperature, a solution in 1:1 toluene/acetonitrile of 6.32 g (0.022 mol) of 2,3-dichloro-4-methanesulfonylbenzoyl chloride freshly prepared with oxalyl chloride is introduced. After stirring briefly, extraction is carried out with a small amount of ethyl acetate against a slightly alkaline-aqueous solution at pH 10. 2,3-Dichloro-4-methanesulfonylbenzoic acid 4-oxobicyclo[3.2.1]oct-2-en-2-yl ester is obtained in the form of an amorphous crystallisate in a yield of 5.5 g (71%). $^1$H-NMR (DMSO-D$_6$): 8.19 ppm, 2H; 5.85 ppm, s, 1H; 3.48 ppm, s, 3H; 3.07 ppm, m, 1H; 2.84 ppm, m, 1 H; 1.9–2.2 ppm, 4H; 1.7 ppm, 2H.

What is claimed is:

1. A process for the preparation of a compound of formula I:

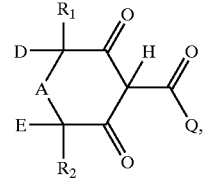

wherein Q is a mono- or poly-substituted phenyl, pyridyl or heteroaryl group so selected that the compound of formula I has a pK value of from 1 to 5;

D is hydrogen or R$_3$;

E is hydrogen or R$_4$;

A is C$_1$–C$_2$alkylene, which may be mono- or poly-substituted by R$_5$; R$_1$, R$_2$, R$_3$, R$_4$ and R$_5$ are each independently of the others hydrogen, C$_1$–C$_4$alkyl, phenyl, C$_1$–C$_4$alkoxy, halogen, hydroxy, cyano, hydroxycarbonyl or C$_1$–C$_4$alkoxycarbonyl;

which comprises a) converting a compound of formula II:

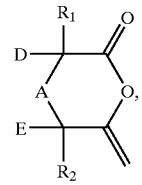

wherein R$_1$, R$_2$, A, D and E are as defined for formula I, either in the presence of an amine base and a catalytic amount of a cyanide or in the presence of an alkali metal alcoholate or alkaline earth metal alcoholate, to a salt of formula III:

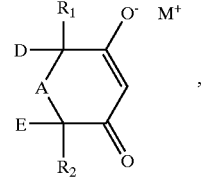

wherein R$_1$, R$_2$, A, D and E are as defined for formula I and M$^+$ is an alkali metal ion, alkaline earth metal ion or ammonium ion, b) reacting that compound with a compound of formula IV:

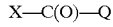

X—C(O)—Q (IV), wherein X is a leaving group and Q is as defined for formula I, to yield a compound of formula V:

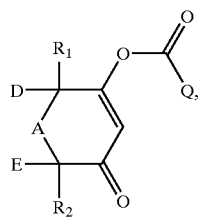
(V)
wherein $R_1$, $R_2$, A, D, E and Q are as defined for formula I, and
c) converting that compound in the presence of catalytic amounts of cyanide ions and in the presence of a base to a compound of formula I.
* * * * *